US008008598B2

(12) United States Patent
Whitman et al.

(10) Patent No.: US 8,008,598 B2
(45) Date of Patent: Aug. 30, 2011

(54) METHOD FOR FORMING STAPLE POCKETS OF A SURGICAL STAPLER

(75) Inventors: Michael P. Whitman, New Hope, PA (US); John E. Burbank, Ridgefield, CT (US); Donald Malinouskas, Monroe, CT (US)

(73) Assignee: Tyco Healthcare Group LP, New Haven, CT (US)

( * ) Notice: Subject to any disclaimer, the term of this patent is extended or adjusted under 35 U.S.C. 154(b) by 166 days.

(21) Appl. No.: 11/494,999

(22) Filed: Jul. 27, 2006

(65) Prior Publication Data
US 2007/0056932 A1 Mar. 15, 2007

Related U.S. Application Data

(60) Provisional application No. 60/703,493, filed on Jul. 27, 2005.

(51) Int. Cl.
*B23K 26/38* (2006.01)

(52) U.S. Cl. .................................. 219/121.69

(58) Field of Classification Search ............... 219/121.7, 219/121.71, 121.82, 121.68, 121.69; 700/166
See application file for complete search history.

(56) References Cited

U.S. PATENT DOCUMENTS

| | | | | |
|---|---|---|---|---|
| 5,197,013 A * | 3/1993 | Dundorf | | 219/121.69 |
| 5,225,650 A * | 7/1993 | Babel et al. | | 219/121.82 |
| 5,239,160 A * | 8/1993 | Sakura et al. | | 219/121.82 |
| 5,829,662 A * | 11/1998 | Allen et al. | | 227/177.1 |
| 6,008,468 A * | 12/1999 | Tanaka et al. | | 219/121.71 |
| 6,300,595 B1 * | 10/2001 | Williams | | 219/121.69 |
| 6,479,787 B1 * | 11/2002 | Jendick | | 219/121.68 |
| 6,486,436 B1 * | 11/2002 | Shah et al. | | 219/121.82 |
| 6,515,253 B1 * | 2/2003 | Battaglia | | 219/121.67 |
| 6,670,575 B1 * | 12/2003 | Wrba et al. | | 219/121.68 |
| 6,775,959 B1 * | 8/2004 | Lasson | | 53/492 |
| 6,829,517 B2 * | 12/2004 | Cheng et al. | | 700/166 |
| 6,953,138 B1 * | 10/2005 | Dworak et al. | | 227/175.1 |
| 7,121,446 B2 * | 10/2006 | Arad et al. | | 227/176.1 |
| 2003/0103107 A1 * | 6/2003 | Cheng et al. | | 219/121.71 |
| 2003/0179687 A1 * | 9/2003 | Schoeppel et al. | | 369/273 |
| 2005/0087521 A1 * | 4/2005 | Yang | | 219/121.69 |

FOREIGN PATENT DOCUMENTS

| | | | |
|---|---|---|---|
| JP | 2000-334524 A | * | 12/2000 |
| JP | 2001-276987 A | * | 10/2001 |
| JP | 2003-311459 A | * | 11/2003 |

OTHER PUBLICATIONS

Machine translation of Japan Patent No. 2003-311,459, Dec. 2009.*
Machine translation of Japan Patent document No. 2001-276,987, May 2010.*

* cited by examiner

*Primary Examiner* — Geoffrey S Evans

(57) ABSTRACT

A system and method for forming a staple pocket, e.g., on the anvil portion of a surgical stapler device. A laser-machining system may include a laser-emitting device that is configured to emit a laser beam or beams for forming staple pockets on the anvil of a surgical stapler. The staple pockets of an anvil may be formed successively or simultaneously. The anvil of the surgical stapler is mounted in a mounting mechanism so as to control its movement, and the laser-emitting device is controlled by a control module, which may control any aspect of the laser-machining operation, e.g., the intensity of the laser beam, the movement of the laser-emitting device relative to the anvil, etc. The control module may be a processor that includes software that provides instructions for the operation of the control module, and may be programmable by a user for inputting parameters, e.g., shape, arrangement, etc., corresponding to the staple pockets.

13 Claims, 6 Drawing Sheets

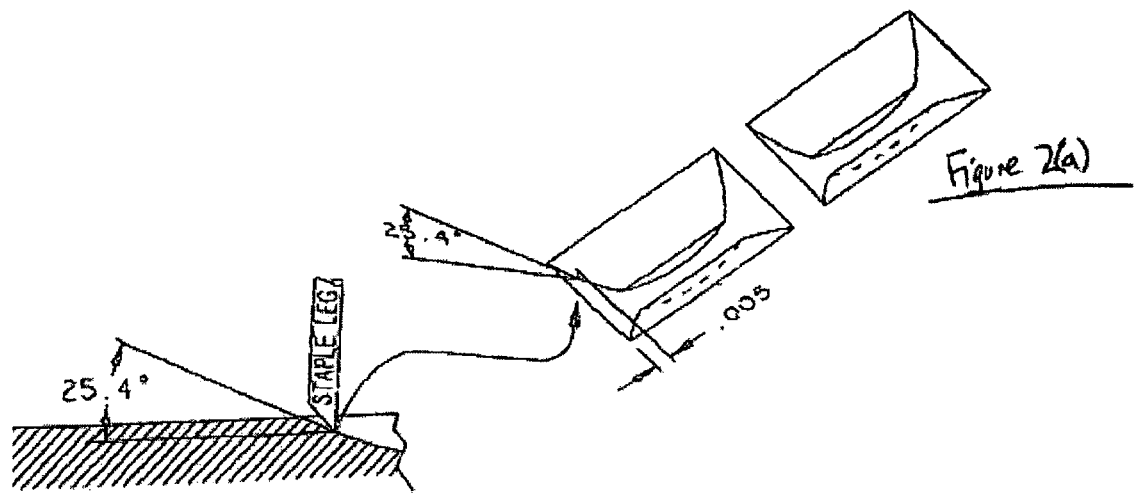
Figure 2(a)
Figure 2(b)
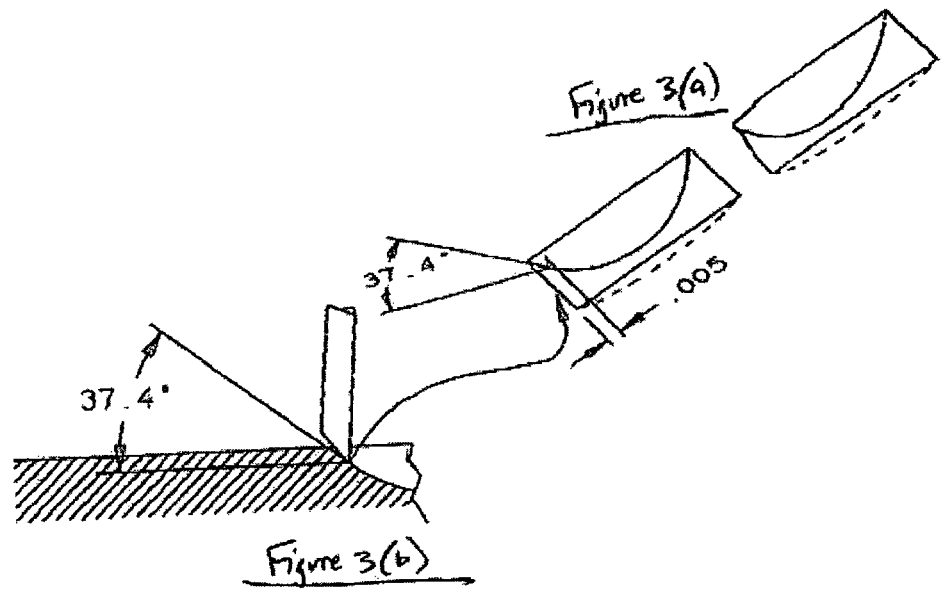
Figure 3(a)
Figure 3(b)

METHOD FOR FORMING STAPLE POCKETS OF A SURGICAL STAPLER

CROSS-REFERENCE TO RELATED APPLICATIONS

This application claims the benefit of U.S. Provisional Patent Application Ser. No. 60/703,493 entitled "System and Method for Forming Staple Pockets of a Surgical Stapler", filed Jul. 27, 2005, which is expressly incorporated herein in its entirety by reference thereto.

FIELD OF THE INVENTION

The present invention relates to a system and method for forming a staple pocket. More specifically, the present invention relates to a system and method for forming a staple pocket on an anvil of a surgical stapler.

BACKGROUND INFORMATION

Surgical staplers typically employ an anvil having staple pockets defined therein. Staples are pushed out of a staple cartridge through a section of tissue and against the staple pockets, the staple pockets being shaped so as to receive and progressively bend the legs of the staple into a closed position. More specifically, upon the firing of a staple firing mechanism of a surgical stapler, the staples are pushed out of the cartridge so that the legs of the staples penetrate a section of tissue and proceed into the respective staple pockets. Continuous operation of a staple firing mechanism causes the staple legs to be received into one end of the staple pocket and to slide along the curved valley of the pocket to bend or form in accordance with the curvature of the staple pocket. Eventually, the legs of each staple are fully bent or formed such that the section of tissue is held between the spine of the staple and the bent staple legs.

One method by which staple pockets are conventionally formed in the anvil of a surgical stapler is by coining. One problem that is encountered by conventional methods of forming surgical staple pockets is that the staple pockets are not sufficiently precisely formed, e.g., they do not satisfactorily meet the small tolerances in alignment, depth and smoothness that are desired in surgical staplers. Also, coining does not remove material from the anvil surface in order to form the staple pockets, but rather moves or pushes the anvil material from one location, e.g., the location at which the staple pocket is to be formed, to another location, e.g., often a location immediately surrounding the staple pocket once the staple pocket is formed. Furthermore, the conventional methods of forming surgical staple pockets in the anvil of the surgical stapler may cause structure fractures of the anvil, thereby damaging the surgical stapler and adversely effecting the operation of the surgical stapler. Still further, the conventional methods of forming surgical staple pockets in the anvil of the surgical stapler may cause the formation of uneven pocket surfaces, causing the surgical stapler to operate ineffectively. Still further, the conventional methods of forming surgical staple pockets in the anvil of the surgical stapler may not provide for the formation of different or complex staple pocket shapes. Still further, the conventional methods of forming surgical staple pockets in the anvil of the surgical stapler do not provide adequate consistency of the staple pockets over time—for instance, a coining tool when used over a period of time to form numerous staple pockets gradually experiences wear which, over time, may result in the formation of different shaped staple pockets over that period of time. Still further, the conventional methods of forming surgical staple pockets in the anvil of the surgical stapler may not permit the shape of a staple pocket to be easily or quickly modified, because, if a different staple pocket shape is desired, a new coining tool must be designed, fabricated and installed in the coining device.

SUMMARY

Example embodiments of the present invention relate to a system and method for forming a staple pocket, e.g., on the anvil portion of a surgical stapler device. In an example embodiment, a laser-machining system includes a laser-emitting device that is configured to emit a laser beam or beams for forming staple pockets on the anvil of a surgical stapler. The staple pockets of an anvil may be formed successively or simultaneously. The anvil of the surgical stapler is mounted in a mounting mechanism so as to control its movement, and the laser-emitting device is controlled by a control module, which may control any aspect of the laser-machining operation, e.g., the intensity of the laser beam, the movement of the laser-emitting device relative to the anvil, etc. The control module may be a processor that includes software that provides instructions for the operation of the control module, and may be programmable by a user for inputting parameters, e.g., shape, arrangement, etc., corresponding to the staple pockets.

BRIEF DESCRIPTION OF THE DRAWINGS

FIG. 2(a) is a bottom perspective view of a staple pocket arrangement on the anvil of a surgical stapler, as may be formed in accordance with an example embodiment of the present invention.

FIG. 2(b) is a cross-sectional view of a portion of the staple pocket illustrated in FIG. 2(a).

FIG. 3(a) is a bottom perspective view of another staple pocket arrangement on the anvil of a surgical stapler, as may be formed in accordance with an example embodiment of the present invention.

FIG. 3(b) is a cross-sectional view of a portion of the staple pocket illustrated in FIG. 3(a).

DETAILED DESCRIPTION

Systems and methods for forming a staple pocket are described herein. In example embodiments of the present invention, a system and method are for forming a staple pocket on the anvil of a surgical stapler. It should be understood that, although example embodiments of the present invention are described herein by way of example in connection with the formation of a staple pocket on the anvil of a surgical stapler, example embodiments of the present invention may also be employed to form staple pockets on other portions of a surgical device or on other types of surgical devices.

Figure 1A:
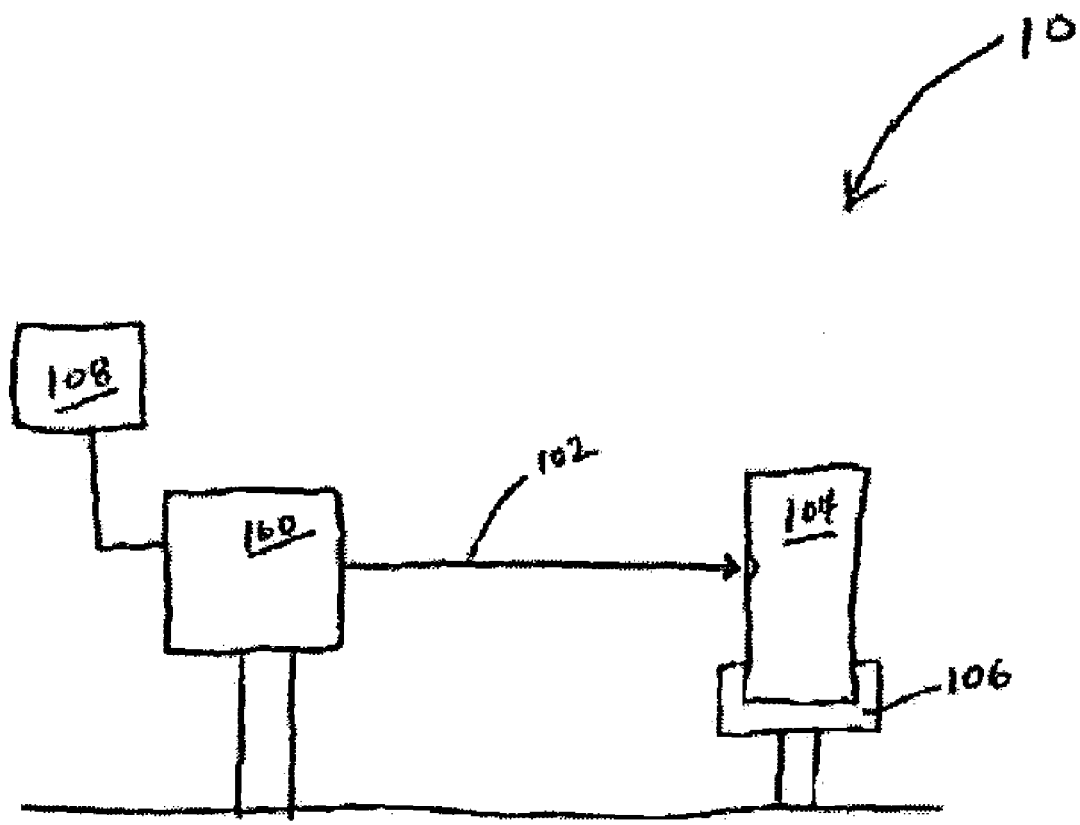
FIG. 1(a) is a diagram that illustrates schematically some of the components of a laser-machining system, in accordance with an example embodiment of the present invention.

According to an example embodiment of the present invention, the staple pockets are formed by a laser. FIG. 1(a) is a diagram that illustrates schematically some of the components of a laser-machining system 10. For instance, FIG. 1(a) illustrates a laser-emitting device 100 that is configured to emit a laser beam 102 (or more than one laser beam 102). The staple pockets of an anvil may be formed successively by a single laser beam 102, or simultaneously by an array of laser beams 102. The laser-emitting device 100, according to an example embodiment, may be a CO2-type laser-emitting device. A workpiece 104, e.g., the anvil of a surgical stapler is mounted in a mounting mechanism 106 so as to control the movement of the workpiece 104. The laser-emitting device 100 is controlled by a control module 108, which may control any aspect of the laser-machining operation. For instance, the control module 108 may control the intensity of the laser beam 102, as well as the movement of the laser-emitting device 100 relative to the workpiece 104. The control module 108 may be a processor that includes software that provides instructions for the operation of the control module 108. In an example embodiment, the control module 108 is programmable by a user for inputting parameters, e.g., shape, arrangement, etc., corresponding to the staple pockets.

The use of a laser to form a staple pocket in the anvil of a surgical stapler, in accordance with the example embodiments of the present invention, may provide advantages over conventional methods of forming such staple pockets. For example, the use of a laser to form a staple pocket in the anvil of a surgical stapler may provide the staple pockets to be more precisely formed as compared to the level of precision that is possible with conventional methods of forming surgical staple pockets. For instance, the conventional method of coining the staple pocket moves or pushes anvil material from one location, e.g., the location at which the staple pocket is to be formed, to another location, e.g., a location immediately surrounding the staple pocket once the staple pocket is formed. Thus, the anvil material may be caused to accumulate in various places on the anvil, e.g., around the edges of the staple pocket so as to thereby form a lip of material at this location. This accumulation of material may adversely effect the operation of the anvil because the accumulated material may interfere with the closure of the staple legs against the anvil. Also, this accumulation of the anvil material may cause uneven or unsmooth surfaces within the staple pockets.

In contrast, by using a laser to form the staple pockets in the anvil, the material of the anvil is not merely moved to another location on the anvil but rather is removed from the anvil by the laser. Thus, there is no accumulated material left on the anvil which could interfere with the operation of the anvil. Furthermore, the use of a laser to form the staple pockets provides the staple pockets to be formed according to small or strict tolerances with respect to the alignment of the staple pockets relative to each other, the depth and curvature of the staple pockets, the smoothness of the surfaces in the staple pocket, etc. Due to the advancement in the miniaturization of surgical instruments in general, and particularly in connection with surgical staplers, this high degree of precision is increasingly important to insure that such surgical instruments operate as desired.

Figure 1B:
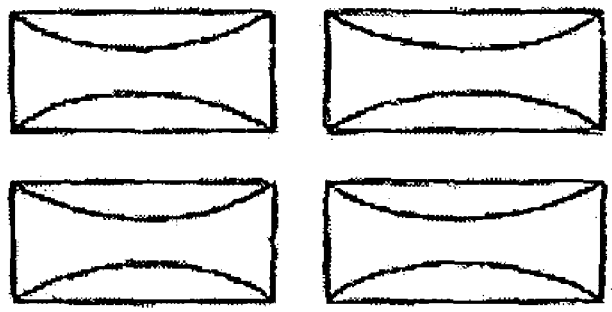
FIG. 1(b) is a top view of a portion of a staple pocket arrangement on the anvil of a surgical stapler, as may be formed in accordance with an example embodiment of the present invention.
Figure 1B:

FIG. 1(b) is a top view of a portion of a staple pocket arrangement on the anvil of a surgical stapler, as may be formed by laser. For purposes of clarity, the staple pocket arrangement is shown on one side, e.g., the upper side, of the knife slot. FIG. 1(b) illustrates staple pockets that are rectangular in shape and that are arranged in parallel rows. Other staple pocket arrangements and staple pocket shapes may also be provided by employing the laser-machining method of example embodiments of the present invention. For instance, FIG. 2(a) is a bottom perspective view of a staple pocket arrangement on the anvil of a surgical stapler. This staple pocket arrangement employs a steep canyon wall near the floor of the canyon which changes to a shallow angle for the rest of the canyon wall. FIG. 2(b) is a cross-sectional view of a portion of the staple pocket illustrated in FIG. 2(a). FIG. 2(b) illustrates the staple leg being received within the staple pocket, e.g., moving in a vertical direction, and prior to the staple leg being bent into a closed position. The angle of 25.4 degrees shown in FIGS. 2(a) and 2(b) is the angle of the surface of the staple pocket relative to the plane of the anvil surface, e.g., the slope angle of the surface along which the staple leg slides when the staple leg is initially received within the staple pocket at a location about 0.005 inches from the longitudinal edge of the staple pocket.

Another staple pocket arrangement that may be provided by employing the laser-machining method is illustrated in FIGS. 3(a) and 3(b). FIG. 3(a) is a bottom perspective view of another staple pocket arrangement on the anvil of a surgical stapler. This staple pocket arrangement also employs a steep canyon wall near the floor of the canyon which changes to a shallow angle for the rest of the canyon wall. FIG. 3(b) is a cross-sectional view of a portion of the staple pocket illustrated in FIG. 3(a). FIG. 3(b) illustrates the staple leg being received within the staple pocket, e.g., moving in a vertical direction, and prior to the staple leg being bent into a closed position. The angle of 37.4 degrees shown in FIGS. 3(a) and 3(b) is the angle of the surface of the staple pocket relative to the plane of the anvil surface, e.g., the slope angle of the surface along which the staple leg slides when the staple leg is initially received within the staple pocket at a location about 0.005 inches from the longitudinal edge of the staple pocket.

Figure 4:
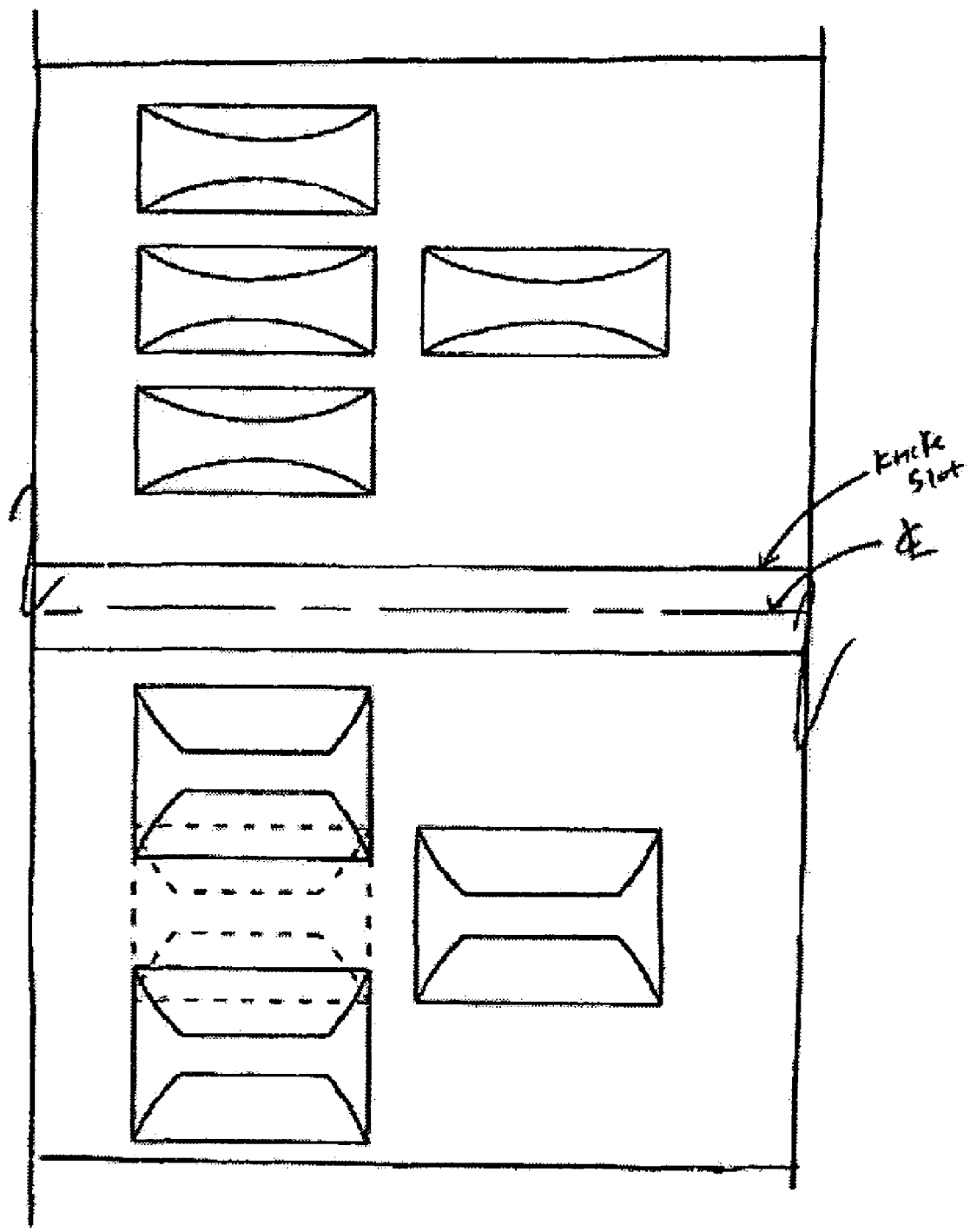
FIG. 4 is a top view of a portion of another staple pocket arrangement on the anvil of a surgical stapler, as may be formed in accordance with an example embodiment of the present invention.

Still another staple pocket arrangement that may be provided by employing the laser-machining method is illustrated in FIG. 4. FIG. 4 is a top view of a portion of a staple pocket arrangement on the anvil of a surgical stapler. In this arrangement, there are three longitudinal rows of the staple pockets located on each side of the knife slot. Of course, it should be understood that any staple pocket shape and arrangement may be formed by lasers in accordance with example embodiments of the present invention.

Furthermore, the use of a laser to form a staple pocket in the anvil of a surgical stapler may also provide an advantage as compared to conventional methods for forming a staple pocket in that the use of a laser may decrease the likelihood that the anvil will be damaged during manufacturing. As set forth above, conventional methods of forming surgical staple pockets in the anvil of the surgical stapler, e.g., coining, may cause structural fractures of the anvil due to the enormous forces that are exerted on the anvil by the coining tool in order to displace the anvil material at the location of the staple pockets. These structural fractures, if undetected prior to the anvil being incorporated into the surgical stapler, may adversely effect the operation of the surgical stapler, e.g., by causing the anvil to fail during use. If these structural fractures are detected prior to the anvil being incorporated into the surgical stapler, the anvil will need to be discarded, leading to wasted materials and increased manufacturing costs. In contrast, the use of a laser to form a staple pocket in the anvil of a surgical stapler may prevent the formation of structural fractures and other types of damage to the anvil.

Still further, the use of a laser to form a staple pocket in the anvil of a surgical stapler, in accordance with example embodiments of the present invention, may provide for the formation of different or complex staple pocket shapes in the anvil of the surgical stapler. As set forth above, conventional methods of forming surgical staple pockets in the anvil of the surgical stapler may not provide for the formation of some staple pocket shapes because, in order to form the staple pockets, the anvil material at the location of the staple pocket must be moved out of the staple pocket location, and the elastic properties of the anvil material may restrict the degree to which the material can be moved. In contrast, the use of a laser to form a staple pocket in the anvil of a surgical stapler removes material from the anvil, rather than merely moving it to a different location on the anvil, and may therefore not be limited by the elastic properties of the anvil material. Consequently, a staple pocket may be formed by a laser in shapes that can not be formed by the conventional staple pocket-forming methods.

Figure 5:
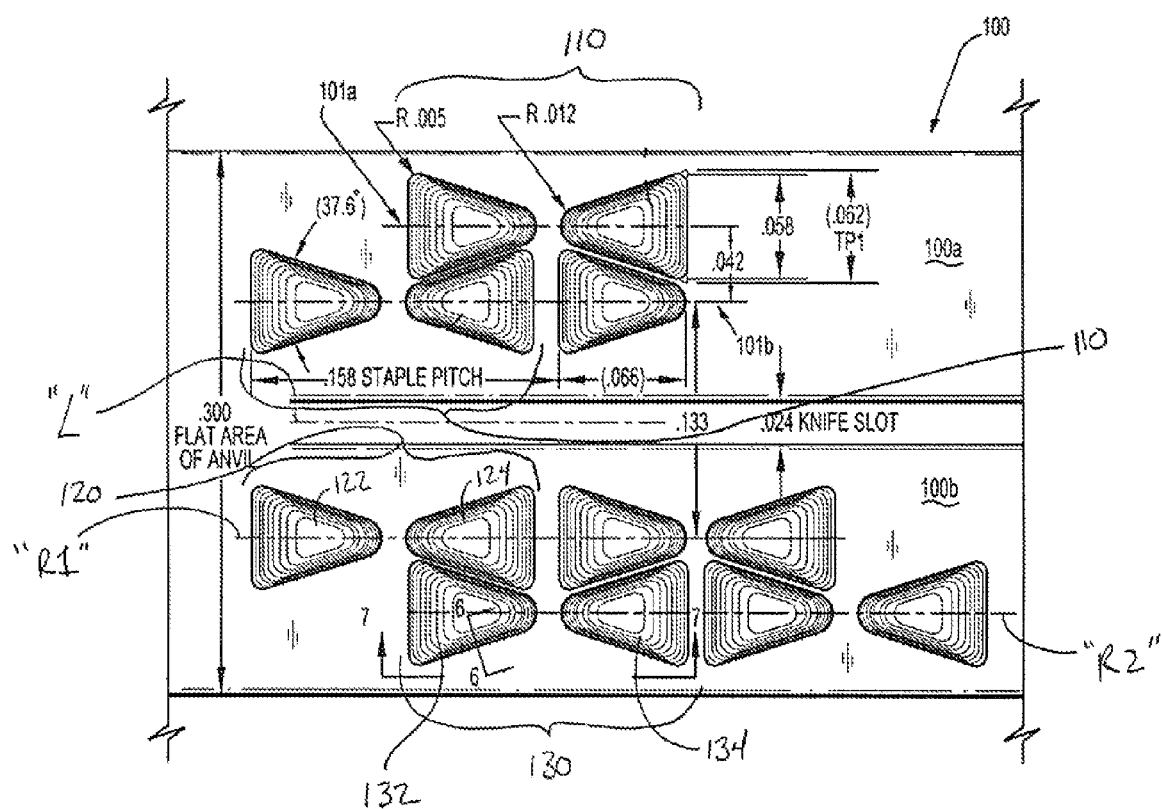
FIG. 5 is a top view of a staple pocket arrangement on the anvil of a surgical stapler, in accordance with an example embodiment of the present invention.
Figure 6:
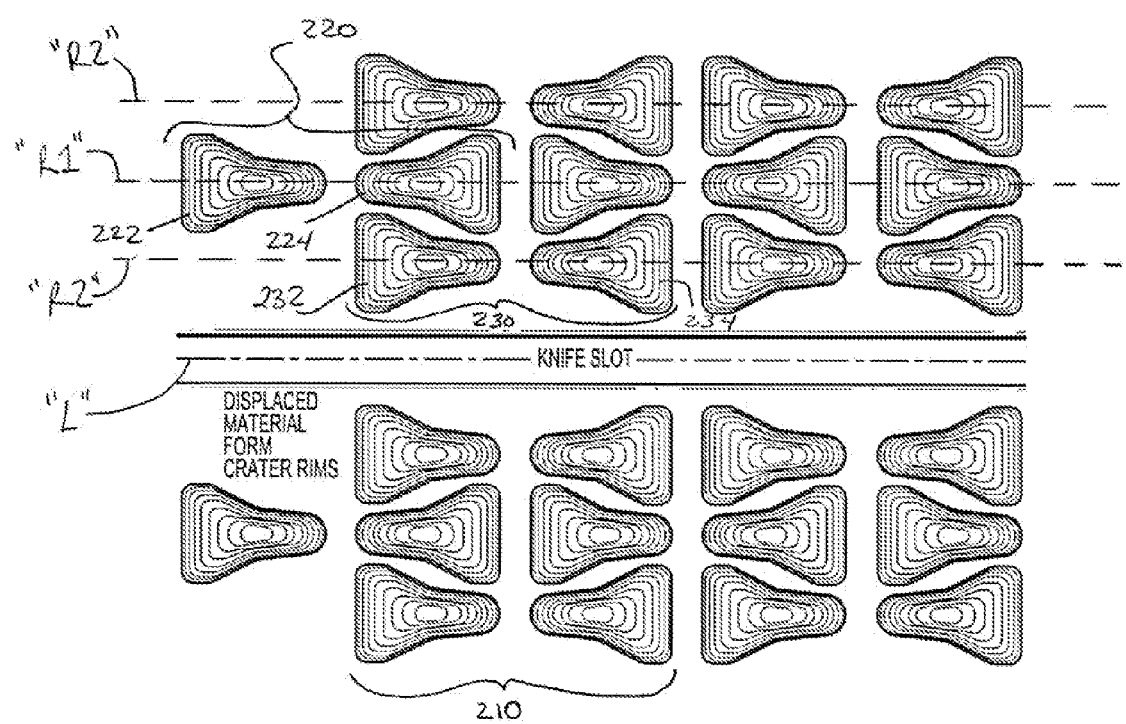
FIG. 6 is a top view of a staple pocket arrangement on the anvil of a surgical stapler, as may be formed in accordance with an example embodiment of the present invention.

FIGS. 5 and 6 illustrate some of the different staple pocket shapes and arrangements that may be formed in accordance with various example embodiments of the present invention. For instance, FIG. 5 is a top view of a staple pocket arrangement on the anvil of a surgical stapler that includes staple pockets 110. Each staple pocket 110, according to an example embodiment, may be roughly triangular in shape when viewed from above. As shown in FIG. 5, one or more first staple pockets 120 are positioned in a first row "R1" and each first staple pocket 120 includes a proximal recess 122 and a distal recess 124 positioned relative to a longitudinal axis "L." With continued reference to FIG. 5, one or more second staple pockets 130 are positioned in a second row "R2" and each second staple pocket 130 includes a proximal recess 132 and a distal recess 134 positioned relative to the longitudinal axis "L." The first row "R1" and the second row "R2" are adjacent one another and may be parallel to each other and the longitudinal axis "L." In the exemplary embodiment, the distal recess 124 of one of the first staple pockets 120 is longitudinally aligned with the proximal recess 132 of one of the second staple pockets 130. Alternatively, as shown in FIG. 6, another example embodiment of a staple pocket arrangement includes staple pockets 210. As shown in this embodiment, one or more first staple pockets 220 are positioned in a first row "R1" and each first staple pocket 220 includes a proximal recess 222 and a distal recess 224 positioned relative to the longitudinal axis "L." With continued reference to FIG. 6, one or more second staple pockets 230 are positioned in one or more second rows "R2" and each second staple pocket 230 includes a proximal recess 232 and a distal recess 234 positioned relative to the longitudinal axis "L." The first row "R1" and the second row "R2" are adjacent one another and may be parallel to each other and the longitudinal axis "L." In the exemplary embodiment, the distal recess 224 of one of the first staple pockets 220 is longitudinally aligned with the proximal recess 232 of one of the second staple pockets 230. Each staple pocket 210 may have a shape when viewed from above that resembles a "bicycle seat", e.g., being generally triangular and having a series of convex and concave curves along its sides. Other shapes may also be employed, and any number of rows of staple pockets may be formed on the anvil of the surgical stapler. Since the staple pockets 110, 210 illustrated in FIGS. 5 and 6 are relatively wide at the longitudinal end at which the staple leg is received, these staple pocket shapes may provide an advantage over other staple pocket shapes in that they may eliminate or at least minimize the likelihood that a staple leg will miss the staple pocket due to, e.g., misalignment between a first jaw of the surgical stapler having the anvil and a second jaw of the surgical stapler having a cartridge configured to fire the staples. Additional aspects of these and other staple pocket shapes and arrangements are described in further detail in U.S. Provisional Patent Application No. 60/703,262, entitled "Staple Pocket Arrangement for Surgical Stapler," filed on Jul. 27, 2005, and U.S. Patent Application Ser. No. 11/495,011, U.S. Patent Publication No. 2007/0057014, entitled "Staple Pocket Arrangement for Surgical Stapler," filed on Jul. 27, 2006, each of which is expressly incorporated herein in its entirety by reference thereto.

The shape and arrangement of these staple pockets shown in FIGS. 5 and 6 provide a row of the staple pockets to be nested with a second, adjacent row of staple pockets. As shown, for instance, in FIGS. 5 and 6, the distance between the nested staple pockets is relatively small so as to minimize the overall width of the anvil. The use of lasers to form these staple pockets provides this relatively small width between the nested staple pockets to be achieved because the staple pockets may be formed precisely with lasers. By comparison, a relatively small width between the nested staple pockets may not be possible to achieve with conventional staple pocket-forming methods because the coining tool that forms a first of the staple pockets may move or push anvil material into the adjacent staple pocket, or else the small amount of anvil material that is intended to be left between the adjacent staple pockets may be destroyed by the forces exerted thereon by the coining tool forming both staple pockets simultaneously. Still further, the use of a laser to form the staple pockets may provide smooth surfaces within the staple pockets, decreasing the likelihood that a staple leg will jam or buckle as it travels along the surface of the staple pocket, and consequently improving the likelihood that the staple will be closed properly.

The use of a laser to form a staple pocket in the anvil of a surgical stapler may also provide an advantage as compared to conventional methods for forming a staple pocket in that the use of a laser may provide the staple pockets to be formed in a consistent shape over time. As set forth above, the conventional methods of forming surgical staple pockets in the anvil of the surgical stapler may not provide adequate consistency of the staple pockets over time, because the use of a coining tool over a period of time causes the coining tool to experience wear which changes the shape of the coining tool. Thus, staple pockets formed by the coining tool at the beginning of the life of the coining tool may have a first shape, while staple pockets formed by the coining tool later in the life of the coining tool, e.g., after the coining tool has experienced wear and has changed shape, may have a second shape that is different from the first shape. In contrast, a laser beam emitted from a laser-emitting device may be consistently applied to an anvil material irrespective of how many times the laser is used, and thus the use of a laser to form a staple pocket in the anvil of a surgical stapler insures that successive staple pockets formed by the laser have a consistent shape.

Still further, the use of a laser to form a staple pocket in the anvil of a surgical stapler may provide the shape of a staple pocket to be easily, quickly and/or inexpensively modified during manufacturing. As set forth above, the conventional methods of forming surgical staple pockets in the anvil of the surgical stapler may not permit the shape of a staple pocket to be easily, quickly and/or inexpensively modified, because, if a different staple pocket shape is desired, a new coining tool must be designed, fabricated and installed in the coining device. Thus, if a change in the shape of a staple pocket is desired, a considerable expense of time and effort must be made in order to generate a new coining tool. In contrast, the operation of the laser-emitting device 100 is controlled by a software of a control module 108, and a change in the shape of a staple pocket may be effectuated by a change of the software or, in the example embodiment whereby the control module 108 is configured to receive user input corresponding to the shape of the staple pocket, by a user providing to the software the different shape parameters of the staple pocket.

It should be appreciated that other machining devices may be provided in place of the laser-emitting device 100. For example, a machining device that removes material during the machining process—as opposed to a machining device that displaces material, e.g., a coining device—may be provided. Examples of such machining devices include EDM (Electrical Discharge Machining) devices, plasma etching devices, etc.

What is claimed is:

1. A method for forming staple pockets, the method comprising the steps of:
    mounting a workpiece;
    emitting a laser beam at the workpiece; and
    forming, via the laser beam, staple pockets on the workpiece in a nested arrangement along a longitudinal axis of the workpiece, the nested arrangement including:
        a first staple pocket positioned in a first row, the first staple pocket having proximal and distal recesses positioned along the longitudinal axis; and
        a second staple pocket positioned in a second row, the second staple pocket having proximal and distal recesses positioned along the longitudinal axis, the second row being parallel to the first row;
    wherein the distal recess of the first staple pocket is axially aligned with the proximal recess of the second staple pocket in a direction orthogonal to the longitudinal axis.

2. The method of claim 1, wherein the workpiece is an anvil of a surgical stapler.

3. The method of claim 1, further comprising the step of moving the workpiece.

4. The method of claim 1, wherein the forming step includes forming one of substantially triangular shaped and bicycle seat shaped staple pocket recesses on the workpiece, the bicycle seat shaped staple pocket recesses being generally triangular and having a convex and concave perimetrical outer profile.

5. The method of claim 4, wherein the forming of the staple pocket recesses on the workpiece is performed successively.

6. The method of claim 4, wherein the forming of the staple pocket recesses on the workpiece is performed simultaneously by simultaneously emitting a plurality of laser beams.

7. The method of claim 1, further comprising the step of controlling the emitting of the laser beam via a control module.

8. The method of claim 7, wherein the control module is a processor that includes software, wherein the method further comprises the step of providing instructions for the operation of the control module.

9. The method of claim 8, further comprising the step of a user programming the control module.

10. The method of claim 9, wherein the programming step includes receiving from the user input parameters.

11. The method of claim 9, wherein the step of receiving from the user input parameters includes receiving at least one of a shape and an arrangement of the staple pocket.

12. The method of claim 7, wherein the controlling step includes controlling an intensity of the laser beam.

13. The method of claim 7, wherein the controlling step includes controlling a movement of the laser beam relative to the workpiece.

* * * * *